(12) United States Patent
Lindh et al.

(10) Patent No.: US 10,216,268 B2
(45) Date of Patent: Feb. 26, 2019

(54) GAZE DETECTION METHOD AND APPARATUS

(71) Applicant: Tobii AB, Danderyd (SE)

(72) Inventors: Fredrik Lindh, Danderyd (SE);
Mattias Gustavsson, Danderyd (SE);
Anders Vennstrom, Danderyd (SE);
Andreas Edling, Danderyd (SE)

(73) Assignee: Tobii AB, Danderyd (SE)

( * ) Notice: Subject to any disclaimer, the term of this patent is extended or adjusted under 35 U.S.C. 154(b) by 34 days.

(21) Appl. No.: 15/171,548

(22) Filed: Jun. 2, 2016

(65) Prior Publication Data

US 2016/0357255 A1 Dec. 8, 2016

(30) Foreign Application Priority Data

Jun. 3, 2015 (GB) .................................. 1509622.5

(51) Int. Cl.
*G06F 3/01* (2006.01)
*A61B 3/113* (2006.01)
*G01C 21/16* (2006.01)
*G05D 1/02* (2006.01)
*G06T 19/00* (2011.01)

(52) U.S. Cl.
CPC ............. *G06F 3/013* (2013.01); *A61B 3/113* (2013.01); *G01C 21/165* (2013.01); *G05D 1/027* (2013.01); *G05D 1/0242* (2013.01); *G05D 1/0244* (2013.01); *G05D 1/0263* (2013.01); *G06T 19/006* (2013.01)

(58) Field of Classification Search
None
See application file for complete search history.

(56) References Cited

U.S. PATENT DOCUMENTS

| 5,802,492 | A | * | 9/1998 | DeLorme | G01C 21/3476 340/990 |
|---|---|---|---|---|---|
| 6,152,563 | A | | 11/2000 | Hutchinson et al. | |
| 2008/0020362 | A1 | * | 1/2008 | Cotin | G09B 23/285 434/267 |
| 2008/0181452 | A1 | | 7/2008 | Kwon et al. | |
| 2014/0164056 | A1 | * | 6/2014 | Johnson | G06Q 30/0201 705/7.29 |
| 2016/0026242 | A1 | * | 1/2016 | Burns | H04N 9/31 345/633 |
| 2016/0224110 | A1 | * | 8/2016 | Massonneau | G06F 3/012 |
| 2017/0278300 | A1 | * | 9/2017 | Hurter | G06T 15/20 |
| 2017/0302903 | A1 | * | 10/2017 | Ng | H04N 13/0022 |

FOREIGN PATENT DOCUMENTS

WO 2012021967 A1 2/2012
WO 2012082971 A1 6/2012

* cited by examiner

*Primary Examiner* — Christopher Kohlman
(74) *Attorney, Agent, or Firm* — Iandiorio Teska & Coleman, LLP

(57) ABSTRACT

A method for determining if a user's gaze is directed in the direction of a zone of interest in a 3D scene comprises: providing a 3D scene containing a zone of interest; associating a property with the zone of interest; creating a bitmap representing the location of the zone of interest in a projected view of the 3D scene, each pixel of the bitmap to which the zone of interest is projected storing the property of the zone of interest; detecting the direction of the user's gaze; using the bitmap to determine if the detected user's gaze is directed in the direction of the zone of interest.

20 Claims, 3 Drawing Sheets

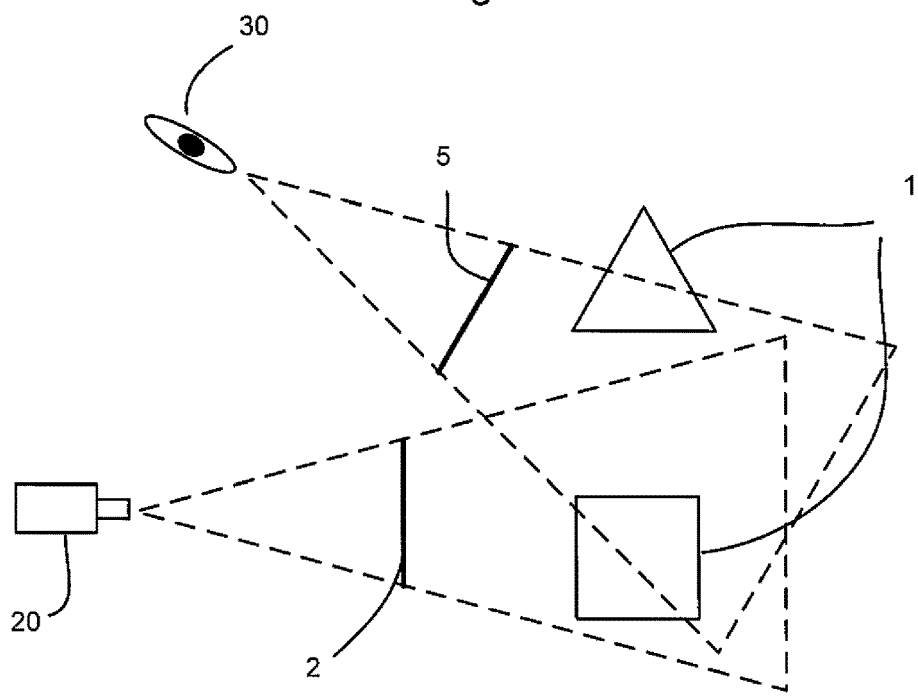
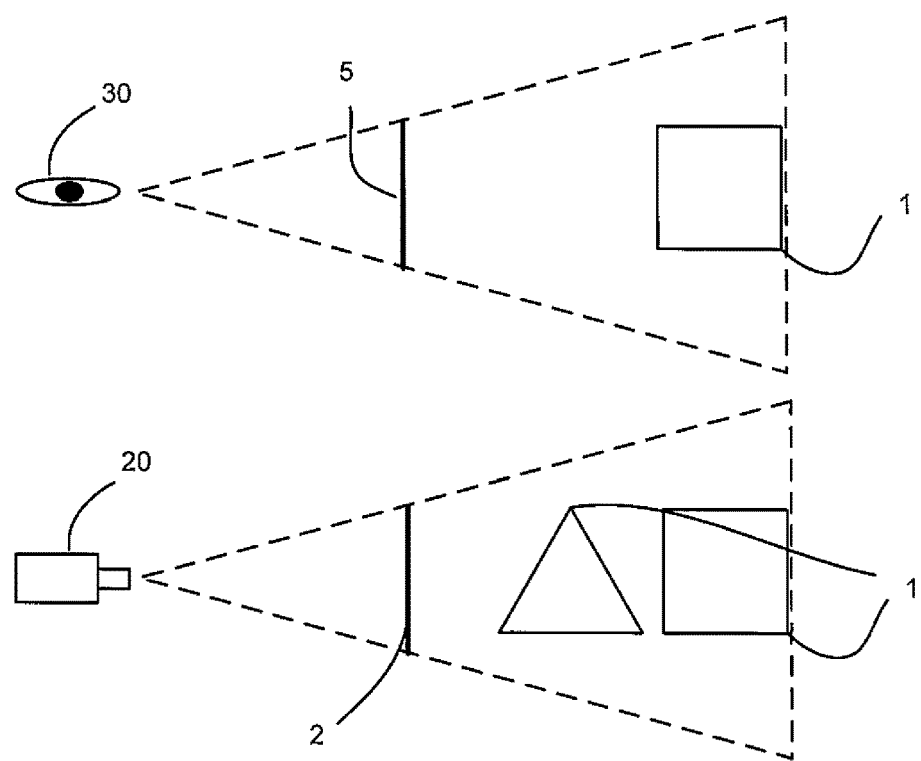

GAZE DETECTION METHOD AND APPARATUS

RELATED APPLICATIONS

This application claims benefit of and priority to U.K. Patent Application No. GB1509622.5 filed Jun. 3, 2015.

The present invention relates to tracking a user's gaze when the user is observing a 3D scene, and in particular how to determine if a user's gaze is directed in the direction of a zone of interest in the 3D scene.

It is known to detect an eye and its gaze direction, this can be done, for example by: illuminating a region in which the eye is sought with infrared radiation; capturing an image of the region; and detecting bright spots in the image that derive from the pupil and cornea of the eye. This approach exploits the bright-eye or "red-eye" effect known to photographers whereby light enters the eye and is reflected or absorbed and re-emitted through the pupil, making the pupil appear brighter than the rest of the eye and the face. A separate, smaller bright spot (also referred to as a glint) is created by the cornea. The relative positions of the pupil and the corneal glint can be used to determine the direction of the gaze of the eye. More details are given in U.S. Pat. No. 6,152,563.

Alternatively, or complimentary, a similar technique may be used whereby infrared illuminators are spaced from an image sensor, thus an image captured by the image sensor has a non-bright pupil, otherwise known as a "dark pupil" effect.

This gaze tracking technology may be implemented in a remote gaze tracker located adjacent a display for example, or in a wearable device such as a pair of glasses, virtual reality headset, augmented reality headset, helmet or the like.

Such gaze tracking technology can be used to determine if a user is looking at a particular object or area on a screen (these objects or areas are generically referred to as 'zones' in the present document). This could be as part of a game, for example. This allows users to interact with images on a screen by looking at them (the act of looking at the image having a predetermined result) or by a combination of looking at an image and another control (e.g. a user pressing a key on a keyboard or mouse whilst their gaze is directed at the image).

Typically, an image on a screen may contain gaze-interactable zones as well as zones which are not gaze-interactable.

Previous methods for determining whether a user's gaze is directed to a gaze-interactable zone in an image tend to be based upon the need for a developer to specify an 'interaction mask' to indicate the location on the screen of the interactable elements. These can work well within certain constraints. Those constraints include use of a static "camera" (i.e. the view point from which the image on the screen is determined), and maintaining a small number of moveable objects that are "occluders" (elements that need to be marked as gaze-interactable, but only for the purpose of transmitting visual culling information, not to be "interactable" per se themselves). Also, such systems typically rely on the gaze-interactable objects being visible in the visual scene.

Further, previously it has been possible to poll or otherwise project a line from a virtual camera to determine objects within a scene with which it intersects. However due to an inherent lack of 100% accuracy in gaze tracking technology, it is preferable to poll an area of a scene so as to account of an error or offset in a user's determined gaze location. In effect this requires searching within a cone shape projected from the virtual camera. This is a processing intensive and inefficient solution.

However, in 3D, where the camera can rotate through a scene, such as in many computer games or in virtual reality headsets, and there is typically an abundance of geometry defining a scene which can act as occluders, previous methods are not so successful. Even without occluders, the 3D situation is problematic. Creating the necessary masks to cope with the 3D environment and the varying locations of objects (be they interactors or occluders) from different view points becomes very complex.

This is because, for example, the number of actors (game entities that can interact with the player in an active fashion) in a 3D game is typically much higher than in 2D-applications. This, in effect, means that every object in the scene needs to be considered as a potential occluder. In contrast, the objects actually intended to be gaze-interactable, such as parts of other characters (a character is an actor that can be possessed by either an AI or a player) might comprise as little as 5-10% of each scene. Consequently, ten times or more bandwidth is required for occluders than for gaze-interactable objects. This is inefficient for the implementation and cumbersome to implement for game developers.

Further, some entities in a game scene, such as world geometry (houses, mountains etc.) do not expose render-bounds or physics bounds natively, which means there is a need to project these meshes to the screen to create interactor occluders for them. This can be extremely computationally expensive. Further some of this world geometry is extremely unwieldy (mountains etc.), so to project them in a meaningful way (to get proper occluders) it would become necessary to first employ mesh splitting algorithms before performing any projection. This becomes impractical.

Finally, it can be desirable in certain scenarios to know if a user's gaze is directed to an object or region which is not visually rendered in the image shown on the monitor or screen. For example, the object or region may be invisible, or may no longer be within the bounds of the image displayed on the screen.

Therefore, there is a problem of how to efficiently implement gaze tracking in 3D scenarios. The present invention aims to at least partially overcome this problem.

According to the present invention, there is provided a method for determining if a user's gaze is directed in the direction of a zone of interest in a 3D scene, the method comprising: providing a 3D scene containing a zone of interest; associating a property with the zone of interest; creating a bitmap representing the location of the zone of interest in a projected view of the 3D scene, each pixel of the bitmap to which the zone of interest is projected storing the property of the zone of interest; detecting the direction of the user's gaze; using the bitmap to determine if the detected user's gaze is directed in the direction of the zone of interest.

This method effectively allows for dynamic and efficient generation of an 'interactor mask', in the form of the bitmap. As such, the burden on the game developer is reduced and gaze-interaction can be more readily incorporated into 3D scenarios.

The step of detecting can comprise detecting the direction of the user's gaze relative to the bitmap or another projection of the 3D scene.

The method can further comprise providing a visual representation for the user, corresponding to the 3D scene; and the step of detecting can comprise detecting the direction of the user's gaze within the visual representation.

A viewport for the bitmap and a viewport for the visual representation can be at the same position with respect to the 3D scene. Alternatively, a viewport for the bitmap and a viewport for the visual representation can be not at the same position with respect to the 3D scene. Alternatively, a viewport for the visual representation can be of a second scene corresponding to the 3D scene.

The zone of interest, or part of the zone of interest, may not be visible within the visual representation. The zone of interest, or the part of the zone of interest, may not be visible within the visual representation because it is hidden behind one or more other objects.

The method can further comprise determining that the user's gaze is directed to the zone of interest, or the part of the zone of interest, that is not visible within the visual representation.

There can be multiple zones of interest. Different zones of interests can be associated with different properties. The step of creating can include creating a bitmap with a pixel containing multiple properties of zones of interest, and the step of creating can further comprise allocating the properties in the pixel an index to indicate the relative depth of the zones of interest within the scene. The property can be one of an identifier for the zone of interest, information concerning the motion of the zone of interest, or information concerning the visual importance of the zone of interest. The method can further comprise associating multiple properties with the, or each, zone of interest.

The 3D scene can be a simulated 3D scene.

The bitmap can be created using depth buffer and/or stencil buffer data corresponding to the 3D scene.

The method can further comprise initiating an interaction when it is detected that the user's gaze is directed in the direction of the zone of interest. The interaction need not be over to the user (although it may be), but may take the form of contributing to a statistical analysis for example.

According to another aspect of the invention, there is provided an apparatus for determining if a user's gaze is directed in the direction of a zone of interest in a 3D scene, the apparatus comprising: a buffer configured to store a bitmap representing the location of a zone of interest in a projected view of a 3D scene, each pixel of the bitmap to which the zone of interest is projected storing a property of the zone of interest; a detector for detecting the direction of the user's gaze; a processor for using the bitmap to determine if the gaze detected by the detector is directed in the direction of the zone of interest.

The invention is described below with reference to exemplary embodiments and the accompanying drawings, in which:

FIG. 3 is a diagram illustrating a different use of separate visual and gaze-detection cameras;

FIG. 4 is a diagram illustrating a further use of separate visual and gaze-detection cameras.

The present invention relates to gaze tracking with respect to a 3D scene. The term gaze tracking is used herein to refer to any system that detects and/or monitors the location of an eye and/or the direction of the gaze of an eye. The skilled reader will be aware of, and understand, such systems.

It is also noted that the description also refers to 'gaze-interactable' objects or zones. This phrase is intended to indicate objects that the system can detect a user's gaze being directed towards. This may or may not lead to an overt 'interaction' for the user. For example, the user may see no sign when a system detects their gaze being directed at a gaze-interactable object. However, the fact that the object has been looked at will have been detected and may be used by the system (e.g. for statistical analysis) in a non-overt manner. Therefore, the term 'gaze-interactable' should not be interpreted to require an overt interaction with the user.

Figure 1:
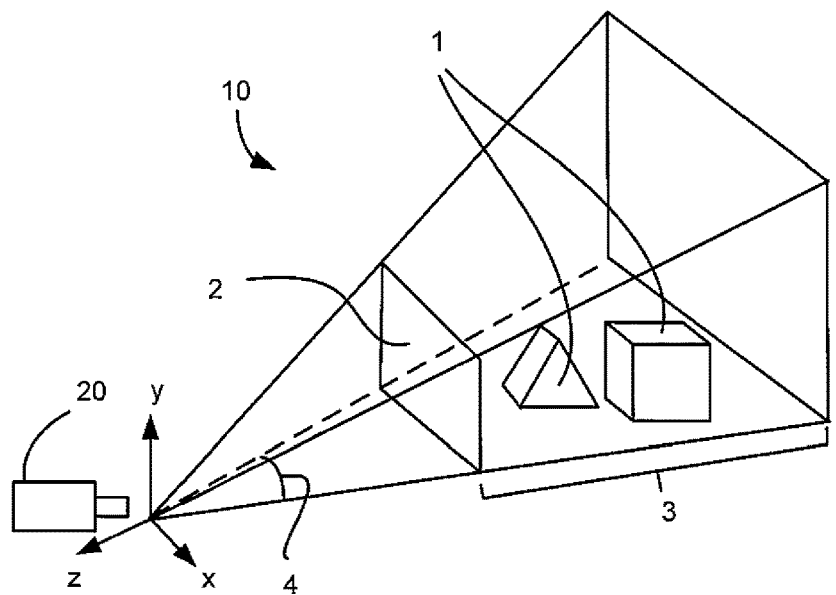
FIG. 1 is a diagram for explaining how 3D scenes are rendered as a 2D image.

FIG. 1 provides an example of a 3D scene. Such a scene can be a virtual 3D scene 10, such as in a computer game or created for a virtual reality headset. The scene 10 contains 3D objects 1. Such objects 1 may move within the scene 10 over time. Indeed, the objects 1 may also move out of the scene 10 and other objects 1 may move into the scene. When such 3D scenes are viewed on a monitor or computer screen, the monitor or screen presents a 2D image representing a view on the 3D scene from a particular location in space, through a viewport 2. The viewport 2 delimits the image that would be seen by a camera or eye located at a notional position with respect to the 3D scene 10. The combination of the camera position and the viewport 2, sets the field of view 4. FIG. 1 also shows the view frustum 3, which is the region of the 3D scene 10 (i.e. extending to the rearmost part of the 3D scene 10) that is shown in the viewport 2.

The FIG. 1 diagram also applies to stereoscopic images, such as used in virtual reality headsets for example. In that case, each eye of a user is presented with a slightly different viewport onto a scene, from which the user's brain then perceives a single 3D image. In this case each image is usually deformed in a non-linear fashion to compensate for lens characteristics. However, the underlying concepts are the same as discussed with reference to FIG. 1 for each image presented to each of the user's eye.

The 3D objects 1 may be notionally infinitely complex 3D shapes, constructed from polygons. The image viewed via the viewport 2 is a 2D projection of the 3D objects 1 onto the plane of the viewport 2 as seen from the camera position, as discussed above. However, the screens on which the 2D viewport 2 images are displayed are composed of arrays of discrete elements or pixels. As such, the projections of the 3D objects 1 must be rasterized onto a display grid, by sampling the projected image at each of the screen pixel locations, to produce the image that will be presented as the visual scene (i.e. the scene observed through the viewport 2). The pixel values are stored in a memory area or buffer, as a 2D "bitmap" corresponding to the same dimensions as the screen or viewport 2.

It is noted that the term "bitmap" has a number of possible meanings. In the context of the present invention, and as is common in the field of computer graphics, it is used to refer to the concept of a spatially mapped array of pixels, which can also be known as a "pixmap". The term bitmap is not intended to convey any limitation in terms of the bit depth of the stored information. In the present invention, the bit depth of the stored information can be variable.

The present invention utilizes a bitmap that specifically stores information about the gaze-interactable zones in a 3D scene 10. That bitmap may be combined with a visual bitmap or may be entirely separate. The use of such a bitmap according to the invention is effectively a dynamic and efficient way of generating the 'interaction masks' that a developer would otherwise have to manually specify in the 3D scene. The efficiency is partly achieved because the development of the mask is considered as 'screen space' issue, rather than a 3D scene issue. That is, rather than approaching the problem of specifying the mask as a problem to be solved in the 3D world specified by the developer, as in the past, the starting point for the invention is to realise that gaze-tracking is performed with respect to a 2D window or viewport (typically, but not necessarily, the screen). As such, the 'mask' can be created based upon that 2D window, rather than in the 3D world.

When considering gaze-tracking, not all 3D objects 1 will be gaze-interactable. Therefore, according to the present invention, it is possible to simplify the 3D scene 10 used for gaze-tracking by only considering those zones which are gaze-interactable. This can be used to generate a separate bitmap which can be stored to a buffer for use with the gaze detection system. This is discussed in more detail later.

The bitmap used for gaze detection will correspond to the visual scene observed by the user on the screen in a predetermined way. For example, they could represent the same 3D scene 10 observed from the same camera position through the same viewport (but nonetheless store different information, because the gaze-detection bitmap will only be concerned about properties of gaze-interactable objects, as discussed below). However, that relationship is not the only possibility.

For example, the cameras used for the gaze detection bitmap and the visual scene may be coincident, but the visual scene displayed to the user may not be complete. One example of this could be because the user is using a "picture-in-picture" mode on a television. As such, it may be possible to use the gaze detection bitmap to follow whether a user's gaze is tracking the position of an object as it passes through a region of the screen showing a different, overlaid, image. In another variation, the same object may appear in a different form in the visual and gaze interaction renderings of the 3D scene 10. For example, an object 1 may have an increased size in the gaze interaction rendering, to make it easier for the user's gaze to register as being directed to that object 1. Other different possibilities are discussed below.

Figure 2:
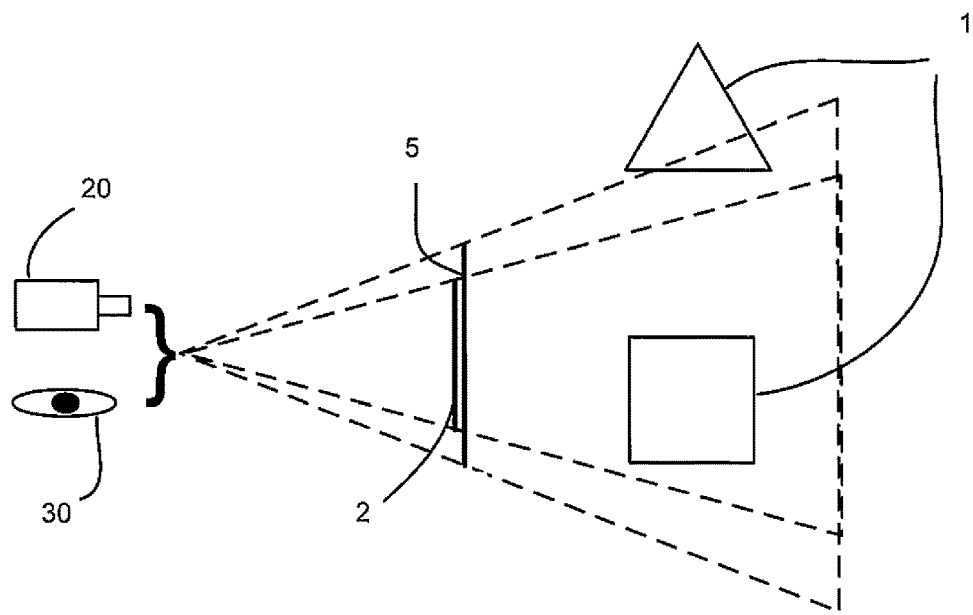
FIG. 2 is a diagram illustrating the use of separate visual and gaze-detection cameras.

In some scenarios, the viewport used for the gaze-interaction bitmap may be different to the visual scene viewport. This could be the case, for example, if it is desired to track whether a user's gaze continues to be directed to an object that moves out of the view frustum 3. In that case the camera for the gaze interaction bitmap may be located at the same notional position as the camera for the visual scene viewport, but the size of the gaze interaction viewport may be larger. This is illustrated in FIG. 2. It is noted that although FIGS. 2-4 illustrate 3D concepts, they are presented as a 2D plan views for simplicity.

In FIG. 2, 3D gaze-interactable objects 1 are viewed from the same location by both the visual camera 20 and the gaze detection camera 30. However, the corresponding gaze detection camera has a wider field of view giving rise to a larger gaze detection viewport 5 compared to the smaller visual scene viewport 2 (N.B. features 2 and 5 are shown slightly separated in FIG. 2 for the sake of clarity, but are considered as coincident for the purposes of the present discussion). Further, there may be other differences in optical parameters between the cameras such as distortion including barrelling, pincushion and the like, depth of focus and resolution etc., As a result, in the visual camera 20 only sees the square 3D object 1, but the triangular 3D object 1 is partly visible to the gaze detection camera through the gaze detection viewport 5. As such, it is possible to determine that a user's gaze would be directed at the triangular object 1, even though it is not visible within the visual viewport 2.

FIG. 3 depicts an alternative possibility, in which the location of the visual scene camera 20 and the corresponding gaze-tracking camera 30 are not coincident. This could be, for example, to take account of an offset between the position and orientation of a screen compared to a user's eyes. In this case, as shown in FIG. 3, not only will different gaze-interactable objects 1 be visible via the different viewports 2, 5 (gaze detection viewport 5 showing both the triangular and the square objects 1, whereas visual viewport 2 shows only the square object 1), but the viewports 2, 5 will also show different projections of the square object 1 as it is being viewed from different angles.

In another scenario, as mentioned above, not all objects within a scene may be gaze-interactable. This is illustrated in FIG. 4. In FIG. 4, only the square object 1 is gaze-interactable, and so this is the only object 1 which is rendered to the viewport 5 of the gaze detection camera 30. However, both the square and the triangular objects 1 are rendered to the corresponding visual viewport 2.

It should be noted that, in the FIG. 4 scenario, the square object 1 is rendered to the gaze detection viewport 5, even though it may not be visible (or is at least partly blocked) in the visual scene because of the positioning of the triangular object 1 between the square object It and the viewport 2. The non-gaze-interactable objects are effectively ignored in the creation of the gaze interaction bitmap.

In practice, in the FIG. 4 scenario, the visual and the corresponding gaze-interactable scene could be rendered entirely independently, for example. Alternatively, objects within a single virtual scene 10 could be provided with properties to identify them as objects that are or are not rendered in one or other of the visual or gaze detection scenes.

Indeed, although not shown in the Figures, there may be elements within a scene that are in fact only gaze-interactable and not apparent in the visual scene. For example, an object may become invisible within the visual scene, but may remain gaze-interactable (i.e. so that a user could attempt to track its progress by extrapolating its previous motion). Alternatively, a 3D scene may contain sectors, areas or regions which are gaze-interactable, but which do not correspond to a specific visual object. For example, a scene in a game may contain a "dangerous" region that will trigger a response if the user's gaze is directed towards it.

The preceding section of the description has discussed various ways in which the visual and gaze interaction cameras 20, 30 may correspond to each other. The following section discussed in greater detail how the gaze interaction bitmap is produced and utilised.

Figure 5:
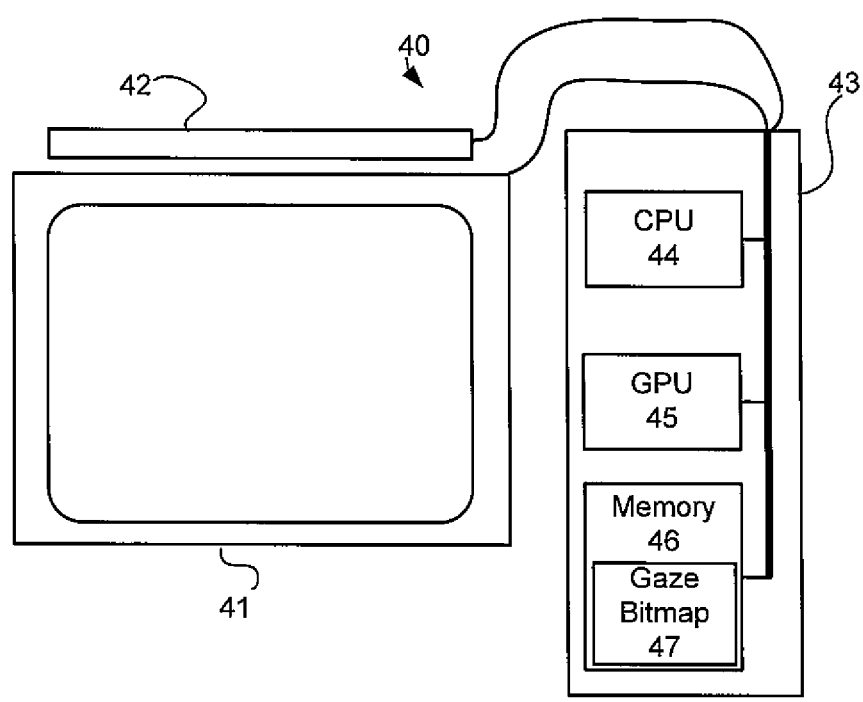
FIG. 5 is a diagram of a system for implement gaze detection.

FIG. 5 shows a schematic view of a system 40 in which the gaze-detection may be implemented. The system 40 includes a screen or monitor 41 and gaze-detector 42. The screen may take a conventional, or non-conventional form including a virtual screen such as a retinal projector or a heads up display in a vehicle. Both the gaze detector 42 and the screen 41 are connected to a computer 43. In modern computers 43, the graphical processing unit (GPU) 45 is often 10-100× faster than the central processing unit (CPU) 44 for parallelizable computations. As such, it is preferable to implement the present invention using the GPU 45. However, the invention could be implemented using any suitable processor such as a CPU 44.

The computer further comprises a memory 46 which contains a buffer into which the gaze detection bitmap 47 can be stored. As mentioned above, the buffer is preferably of variable bit depth. The buffer contains at least enough bit depth to encode one property representative of each gaze-interactable zone 1 (where, as mentioned above, the term "zone" is used to include both 3D objects as well as regions of 3D space) present in the scene 10. In the context of the gaze interaction and visual representation cameras 30, 20 being co-located, and having the same size viewports 5, 2, the buffer could be implemented in conjunction with the visual buffer. In particular, if the visual buffer is implemented in the RGBA format, it is common that there are bits in the alpha channel that are not used. In some implementations of the present invention, those spare bits could be used to store the information relating to zones 1 of interest.

In any case, whatever the specific format used, the buffer is used to store a bitmap 47 representing the viewport 5 onto the 3D scene from the gaze interaction camera 30. The pixels of the bitmap 47, on to which gaze-interactable zones 1 are projected, are used to store a property of the gaze-interactable zones 1.

The property stored in the bitmap 47 may be a unique identifier (ID), identifying the particular gaze-interactable zone. However, this will not always be the case. For example, the idea of having "dangerous" zones in a scene 10 has been previously discussed. In that case, there may be no need to distinguish between individual "dangerous" regions, as opposed to identifying that the user's gaze has been directed at (any) one of the "dangerous" areas. In that case, the information stored in the bitmap may simply represent that the region has the "dangerous" property without any unique ID.

The pixels of the bitmap 47 may be used to store information about more than one property of the zones of interest. For example, in combination with (or instead of) a unique ID, it may be desirable to store other information related to gaze interaction.

Such gaze interaction information could be metadata associated with an object 1, for example indicating the relative visual importance of an object 1. This information can be used to assist in algorithms for detecting whether a user is looking at a particular object if two gaze-interactable objects 1 are located near to each other: if it is difficult to determine which of the two objects a user is looking at, it may be assumed that the user is looking at the most visually "important" object.

Other useful gaze interaction information that may be stored in the bitmap 47 may also include information about an object's 1 motion, such as its velocity and/or acceleration. This information may be relevant to heuristics weighting the likelihood of a user's gaze being directed at any particular object in a particular area (e.g. a faster moving object being more likely to attract a user's attention). Any other variables used for such weightings may also (or alternatively) be stored in the bitmap 47

Creating the gaze interaction bitmap 47, in addition to the visual scene information, increases computation requirements. One way to save computational expense in the present invention, if required, is to down-sample the size of the gaze interaction bitmap 47 (i.e. use less pixels for it)), in comparison to the visual scene, for example. Another alternative would be to specify a subsection of the visual scene that is potentially gaze-interactable (e.g. to ignore menu bars or other constant visual items which might mean that certain areas of the scene will never be visually interactable). This would reduce the computational load (but at the expense of decreased fidelity in the case of down sampling).

As will be apparent from the forgoing discussion, the only items rendered to the gaze interaction bitmap 47 are objects and areas identified as gaze-interactable zones 1. Such objects and areas are pre-defined during the programming/design of the 3D scene 10.

Further, the information stored in the bitmap 47 can include any relevant properties as defined in connection with the gaze-interactable zones 1 when creating the scene 10. In some cases, it may be desirable to store information about multiple objects in the same pixel of the bitmap (i.e. if multiple gaze-interactable objects are aligned behind each other), and in that case an associated index may also be stored, to indicate the order of closeness of the objects with respect to the viewport for example.

Further, at the time of rendering the bitmap 47 based on the projection of the 3D scene 10, any available depth buffer and/or stencil buffer data may be utilised. As such, it is possible to effectively provide a more efficient, and already integrated and supported, substitute for the previous approach to handling occluders and world geometry splitting/projection which can otherwise become troublesome. This approach is possible by considering the 'interaction-mask' in a 2D context, in the same way as the projection of the scene to the viewport, and thus leveraging existing graphics rendering capabilities in the creation of the mask (i.e. the bitmap 47). Once the bitmap 47 has been created and stored, it can be used in conjunction with any eye tracking hardware 42 to determine if a user's gaze is directed to a gaze-interactable zone 1. For example, this could be done by monitoring the user's eyes with respect to a visual scene displayed on the screen 41, but could also be done by monitoring the user's eyes with respect to the viewport 5 for the gaze interaction bitmap 47, or even a separate viewport entirely. So long as the relationship between the various viewports are known, the corresponding scenes 10 from each viewport can be correlated and a determination about the direction of the user's gaze can be made.

Once the direction of the user's gaze is determined, the gaze interaction bitmap 47 can be used to determine if the gaze is directed to a gaze-interactable zone 1, by referencing the property information stored in the bitmap 47. Any information relating to the properties of a gaze-interactable zone 1 to which the user's gaze is directed can then be used to determine the consequence of the user looking at the particular zone 1.

As discussed above, the present invention allows for efficient determination of whether a user is looking at a gaze-interactable object in a 3D scene, by effectively rendering a gaze interaction scene. The information relating to the gaze-interactable scene can be used, for example, in conjunction with the visual scene, to determine the consequences of the direction of the user's gaze.

The invention claimed is:

1. A method for determining if a user's gaze is directed in the direction of a zone of interest in a 3D scene, the method comprising:
    providing a 3D scene containing a zone of interest;
    associating a property with the zone of interest;
    creating a bitmap representing a projected view of the 3D scene containing the zone of interest, each pixel of the bitmap to which the zone of interest is projected storing the property of the zone of interest;
    detecting the direction of the user's gaze;
    using the bitmap to determine if the detected user's gaze is directed in the direction of the zone of interest.

2. A method according to claim 1, further comprising:
    wherein the step of detecting comprises detecting the direction of the user's gaze relative to the bitmap or another projection of the 3D scene.

3. A method according to claim 2, further comprising:
    providing a visual representation for the user, corresponding to the 3D scene; and wherein the step of detecting comprises detecting the direction of the user's gaze within the visual representation.

4. A method according to claim 3, wherein a viewport for the bitmap and a viewport for the visual representation are at the same position with respect to the 3D scene.

5. A method according to claim 3, wherein a viewport for the bitmap and a viewport for the visual representation are not at the same position with respect to the 3D scene.

6. A method according to claim 3, wherein a viewport for the visual representation is of a second scene corresponding to the 3D scene.

7. A method according to claim 3, wherein the zone of interest, or part of the zone of interest, is not visible within the visual representation.

8. A method according to claim 7, wherein the zone of interest, or the part of the zone of interest, is not visible within the visual representation because it is hidden behind one or more other objects.

9. A method according to claim 7, further comprising determining that the user's gaze is directed to the zone of interest, or the part of the zone of interest, that is not visible within the visual representation.

10. A method according to claim 1, wherein there are multiple zones of interest.

11. A method according to claim 10, wherein different zones of interest are associated with different properties.

12. A method according to claim 10, wherein the step of creating includes creating a bitmap with a pixel containing multiple properties of zones of interest, and the step of creating further comprises allocating the properties in the pixel an index to indicate the relative depth of the zones of interest within the scene.

13. A method according to claim 1 wherein the property is one of an identifier for the zone of interest, information concerning the motion of the zone of interest, or information concerning the visual importance of the zone of interest.

14. A method according to claim 1, further comprising associating multiple properties with the zone of interest.

15. A method according to claim 1, wherein the 3D scene is a simulated 3D scene.

16. A method according to claim 1, wherein the bitmap is created using depth buffer and/or stencil buffer data corresponding to the 3D scene.

17. A method according to claim 1, wherein the bitmap further undergoes a non-linear deformation.

18. A method according to claim 1, further comprising initiating an interaction when it is detected that the user's gaze is directed in the direction of the zone of interest.

19. An apparatus for determining if a user's gaze is directed in the direction of a zone of interest in a 3D scene, the apparatus comprising:
a buffer configured to store a bitmap representing a projected view of a 3D scene containing a zone of interest, each pixel of the bitmap to which the zone of interest is projected storing a property of the zone of interest;
a detector for detecting the direction of the user's gaze;
a processor for using the bitmap to determine if the gaze detected by the detector is directed in the direction of the zone of interest.

20. An apparatus according to claim 19, wherein the processor is further configured to initiate an interaction when it is detected that the user's gaze is directed in the direction of the zone of interest.

* * * * *

UNITED STATES PATENT AND TRADEMARK OFFICE
CERTIFICATE OF CORRECTION

PATENT NO. : 10,216,268 B2
APPLICATION NO. : 15/171548
DATED : February 26, 2019
INVENTOR(S) : Lindh et al.

It is certified that error appears in the above-identified patent and that said Letters Patent is hereby corrected as shown below:

On the Title Page

Item (72), the inventor's surname:
Vennstrom
Should be changed to:
--Vennström--.

Signed and Sealed this
Twenty-ninth Day of October, 2024

Katherine Kelly Vidal
*Director of the United States Patent and Trademark Office*